United States Patent [19]
Rotzsche et al.

[11] Patent Number: 5,928,956
[45] Date of Patent: Jul. 27, 1999

[54] METHOD OF EXAMINING SILANE-TREATED, INORGANIC MATERIALS

[75] Inventors: Harald Rotzsche, Piding; Klaus-Peter Ditscheid, Troisdorf, both of Germany

[73] Assignee: Huels Aktiengesellschaft, Marl, Germany

[21] Appl. No.: 08/623,011

[22] Filed: Mar. 28, 1996

[30] Foreign Application Priority Data

Apr. 13, 1995 [DE] Germany .............................. 195 14 033

[51] Int. Cl.$^6$ .......................... G01N 21/72; G01N 30/02; G01N 33/00
[52] U.S. Cl. .............................. 436/155; 436/161; 436/72
[58] Field of Search ..................................... 436/155, 161, 436/72

[56] References Cited

U.S. PATENT DOCUMENTS

| | | | |
|---|---|---|---|
| 5,070,116 | 12/1991 | Seyferth et al. | 523/22 |
| 5,086,146 | 2/1992 | Liles et al. | |
| 5,093,153 | 3/1992 | Brochot et al. | 427/41 |

FOREIGN PATENT DOCUMENTS

| | | |
|---|---|---|
| 0 588 505 | 3/1994 | European Pat. Off. |
| 39 30 654 | 3/1990 | Germany |

OTHER PUBLICATIONS

Chem Abstracts, Bigois et al, vol. 85, p. 564, CA 85:13492s.
Patent Abstracts of Japan, AN 90–316608, JP 2–222 335, Sep. 7, 1990.
Patent Abstracts of Japan, AN 91–322772, SU 1–608 573, Nov. 23, 1990.
Jehuda Yinon, et al., Journal of Chromatography A, vol. 688, pp. 231 to 242, Thermal Decompostion Characterization of Explosives by Pyrolysis–Gas Chromatography–Mass Spectrometry, 1994.

*Primary Examiner*—Avis M. Davenport
*Attorney, Agent, or Firm*—Oblon, Spivak, McClelland, Maier & Neustadt, P.C.

[57] ABSTRACT

The invention relates to a method of examining inorganic materials which are treated with organosilicon compounds, wherein the sample material is pyrolyzed within a few seconds and the pyrolysis products are analyzed on-line by gas chromatography on a PLOT column (porous layer open tubular column).

15 Claims, 13 Drawing Sheets

FIG. 1.1
FIG. 1.2
FIG. 1.3
FIG. 1.4

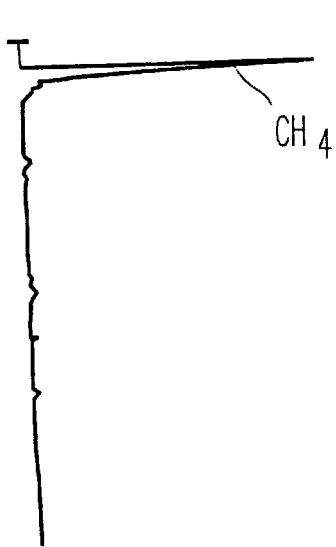
*FIG. 2.1*
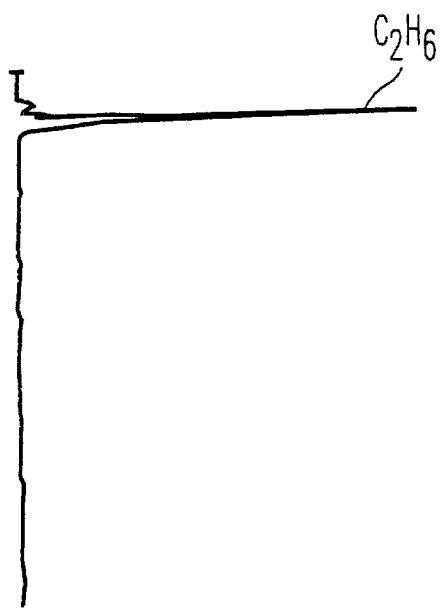
*FIG. 2.2*
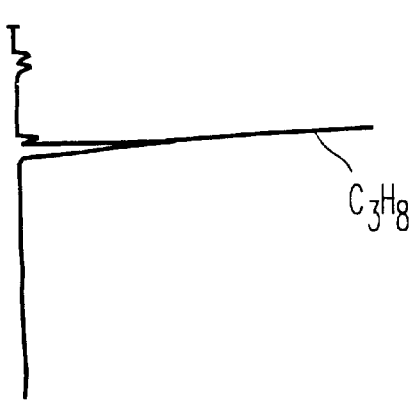
*FIG. 2.3*
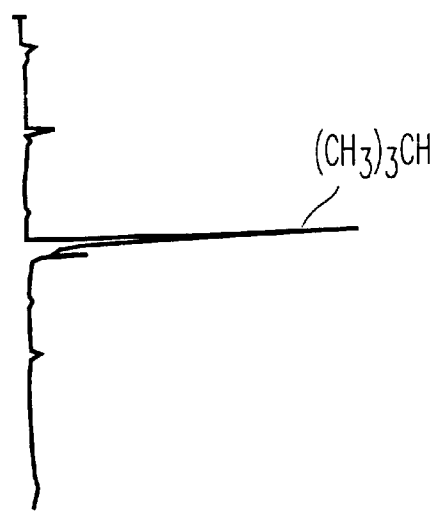
*FIG. 2.4*

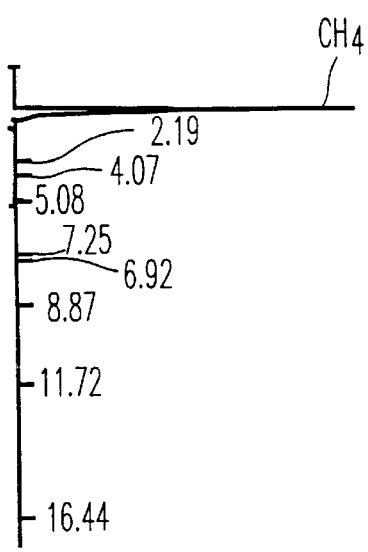
FIG. 3.1
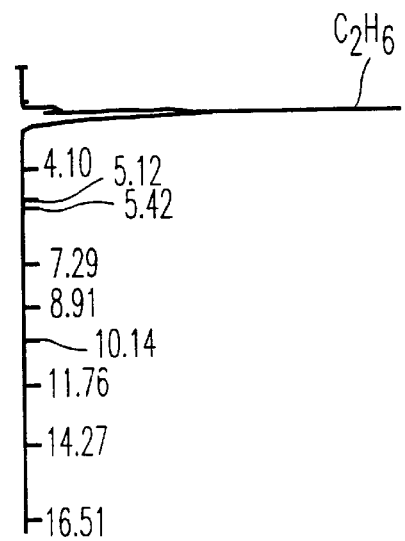
FIG. 3.2
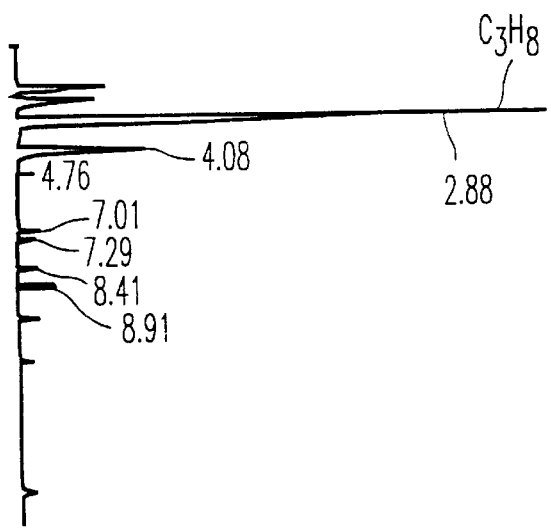
FIG. 3.3
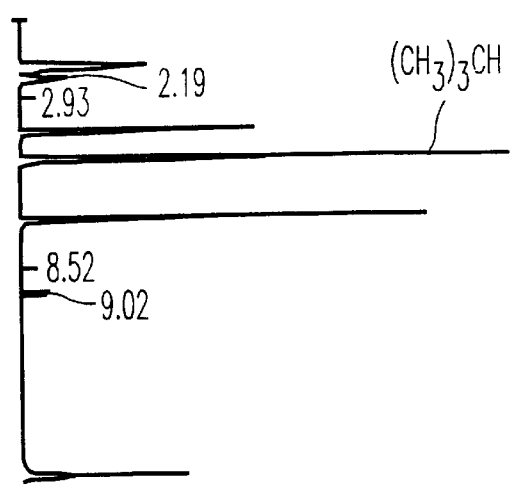
FIG. 3.4

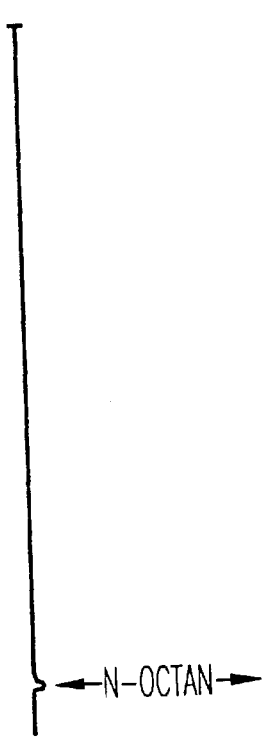
←N-OCTAN→
FIG. 4.1
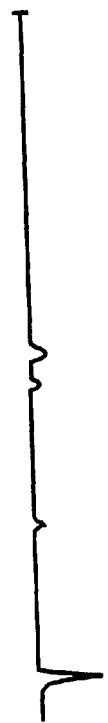
FIG. 4.2
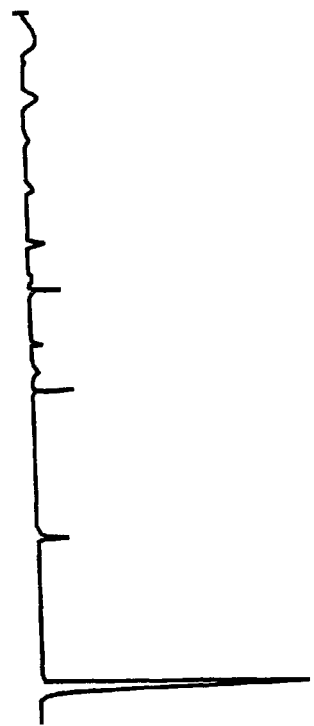
FIG. 4.3
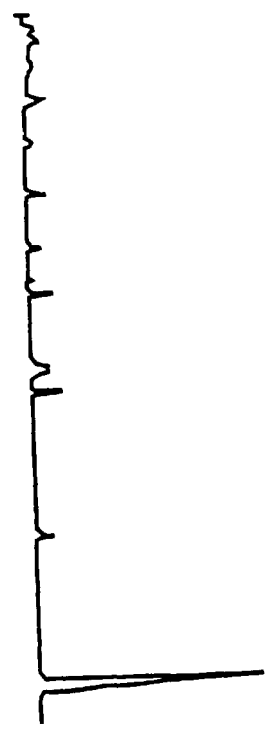
FIG. 4.4
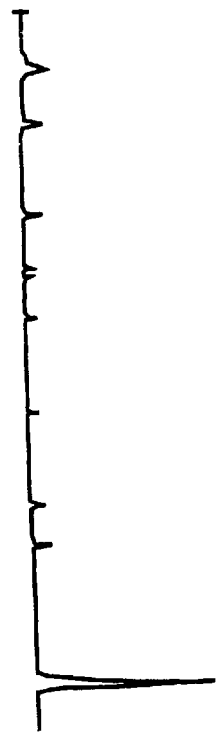
FIG. 4.5

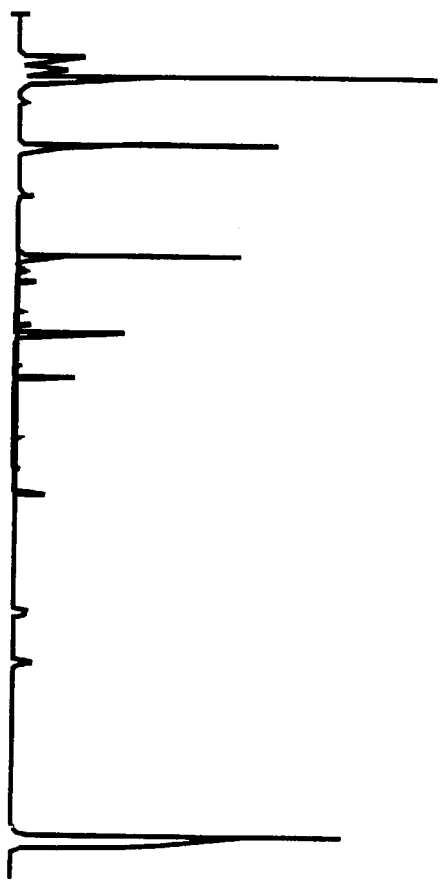
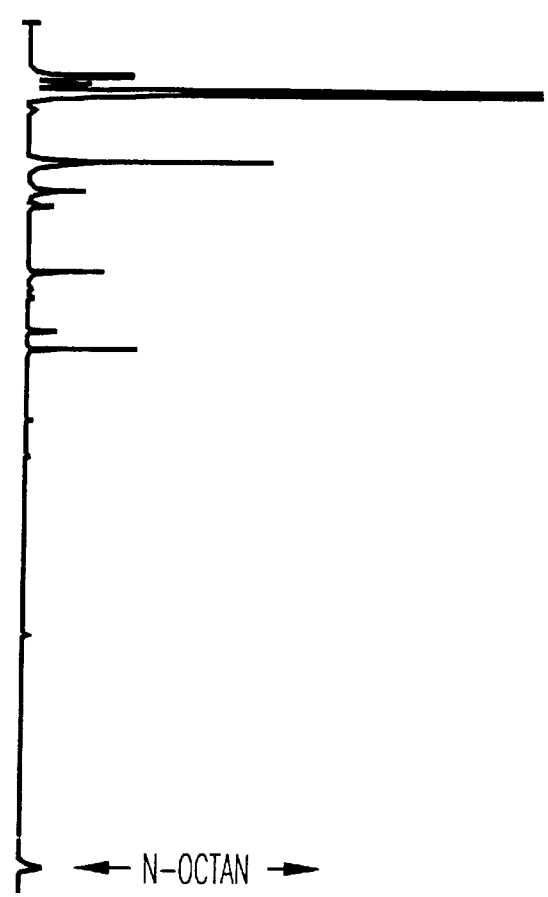
FIG. 4.6  FIG. 4.7

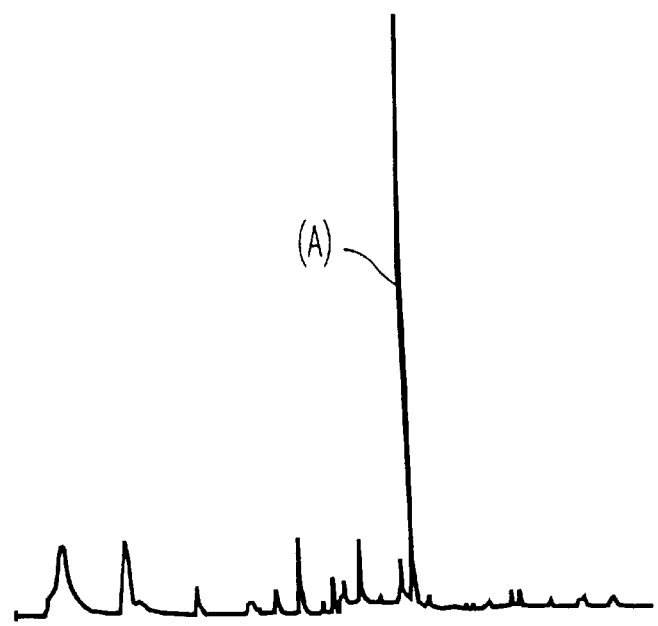
FIG. 5.1
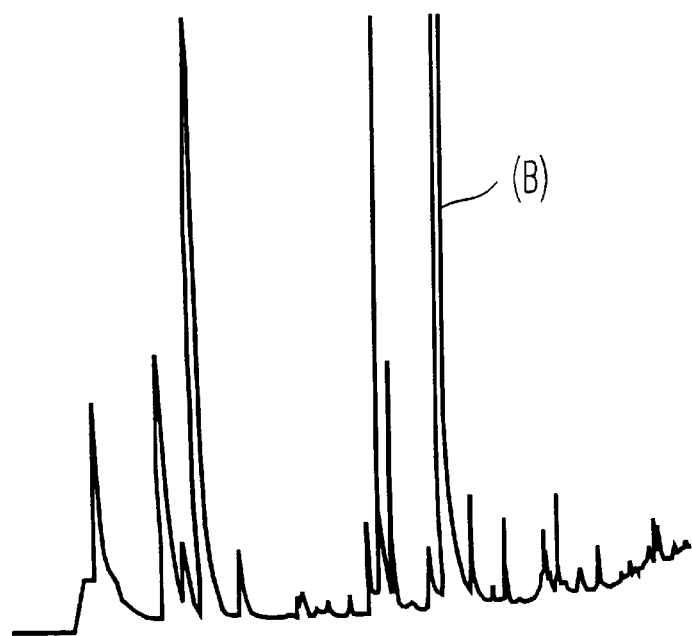
FIG. 5.2

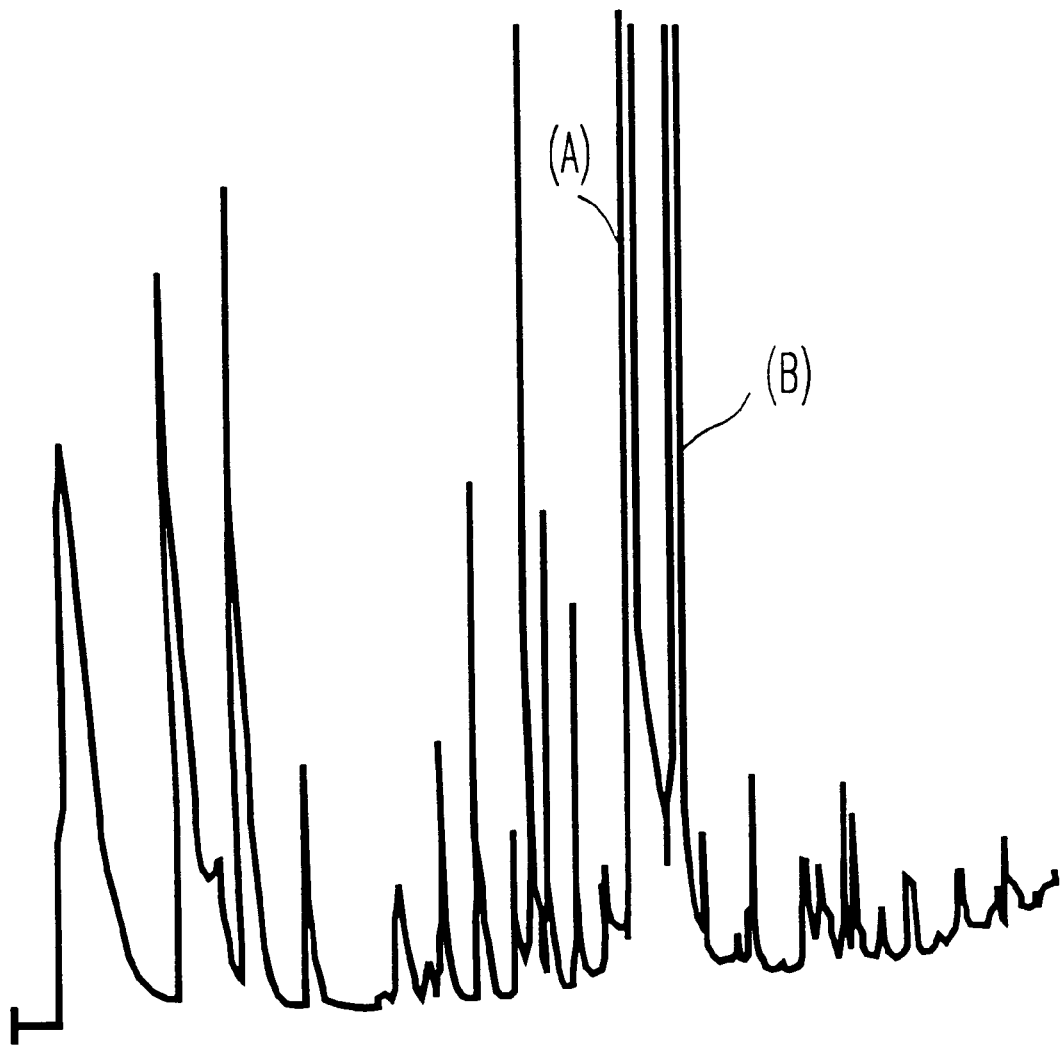
FIG. 5.3

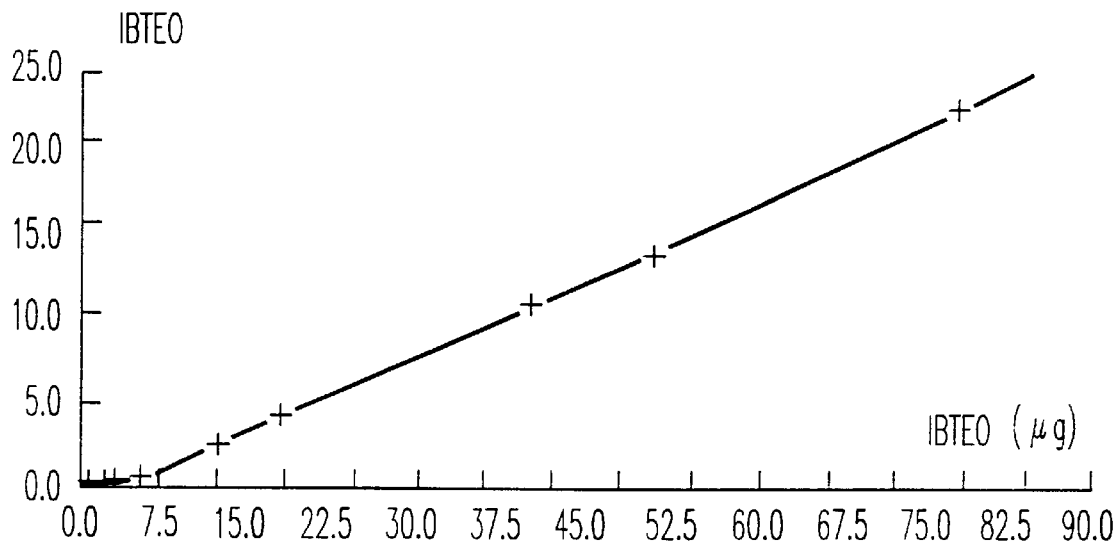
FIG. 6.1
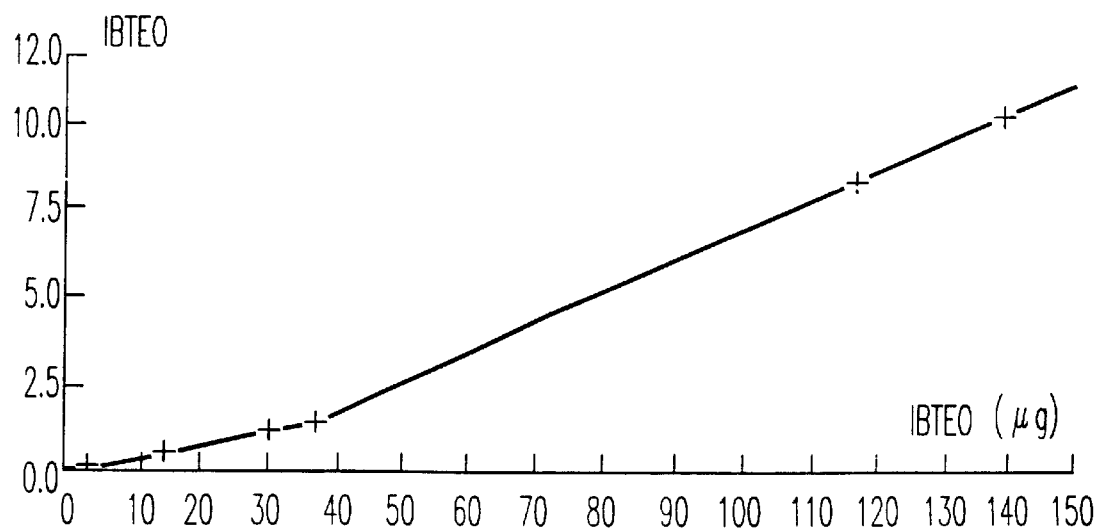
FIG. 6.2

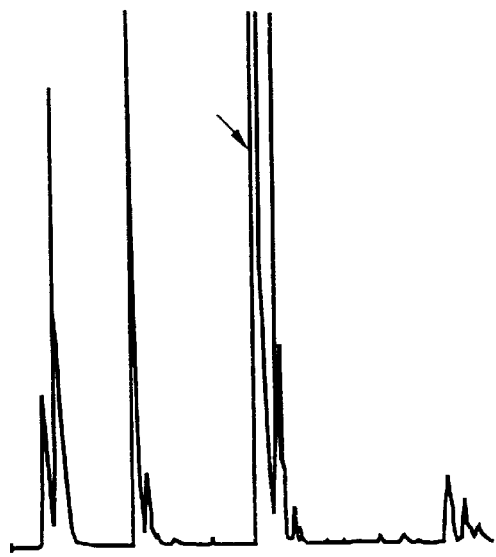
FIG. 8.1
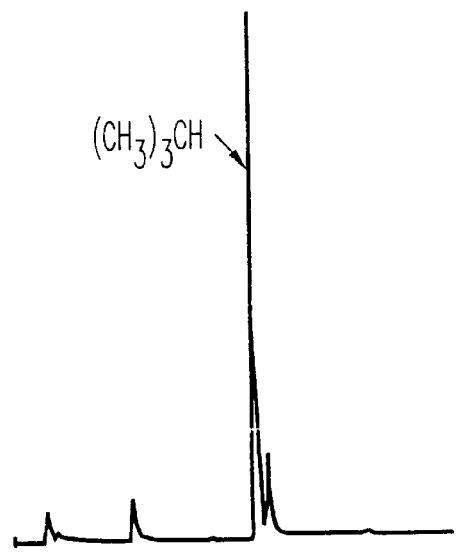
FIG. 8.2
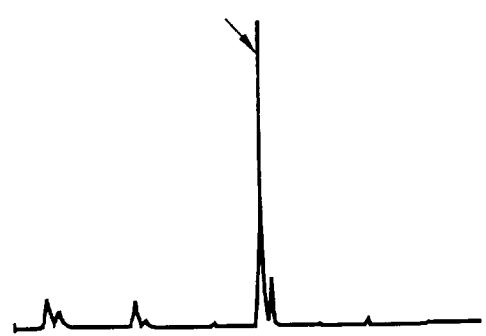
FIG. 8.3
FIG. 8.4

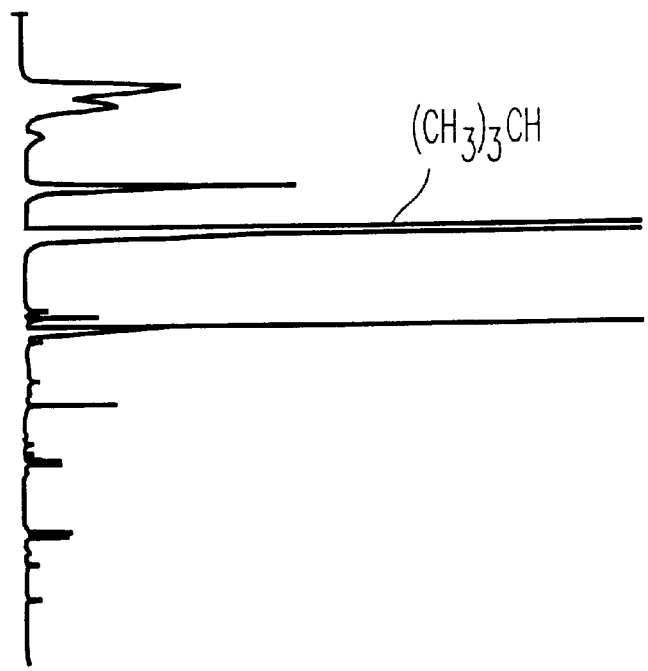
FIG. 9.1
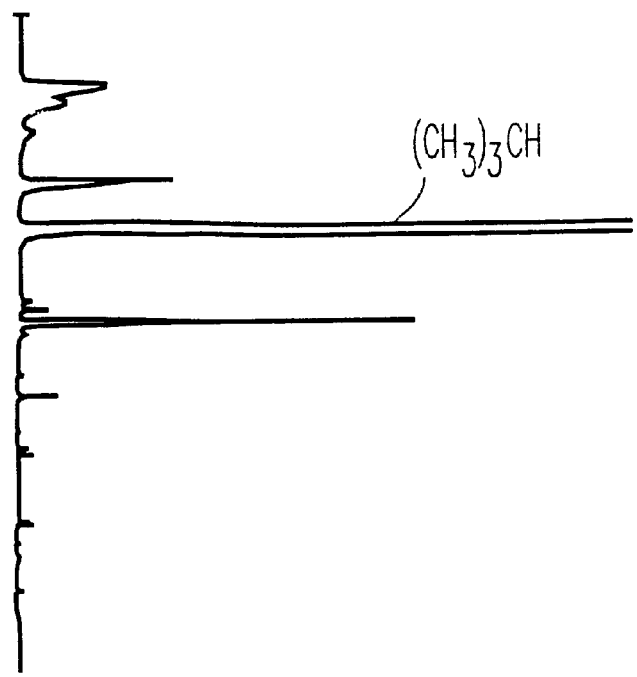
FIG. 9.2

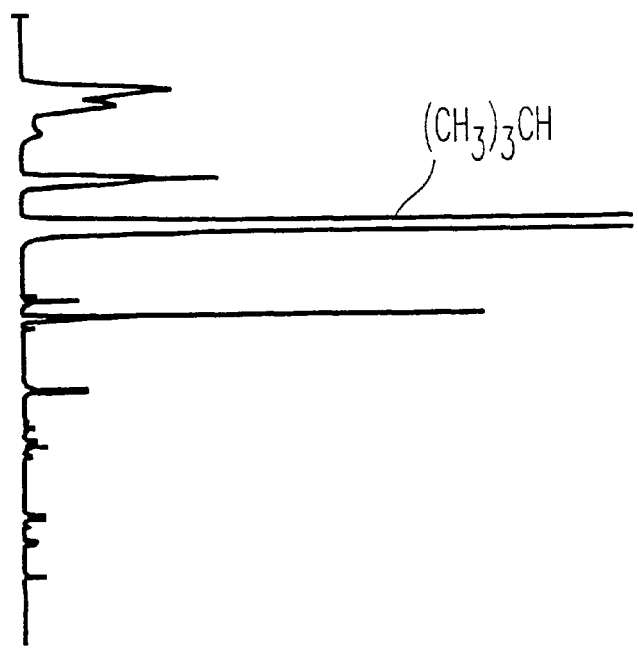
*FIG. 9.3*
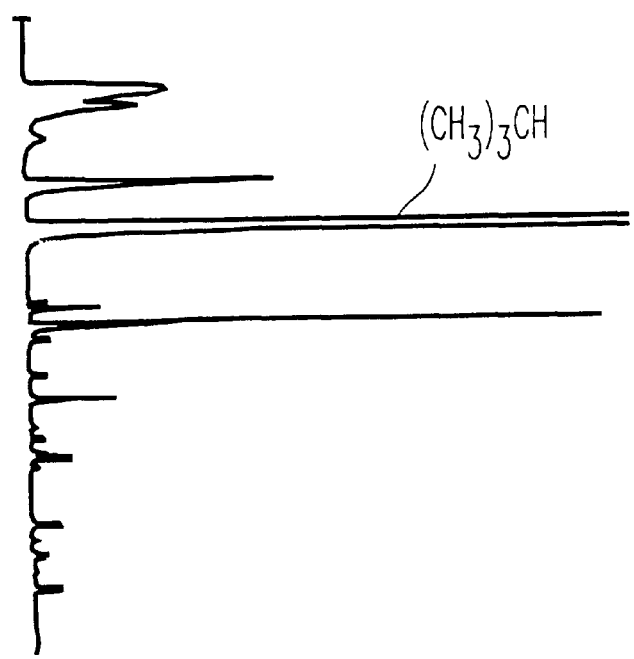
*FIG. 9.4*

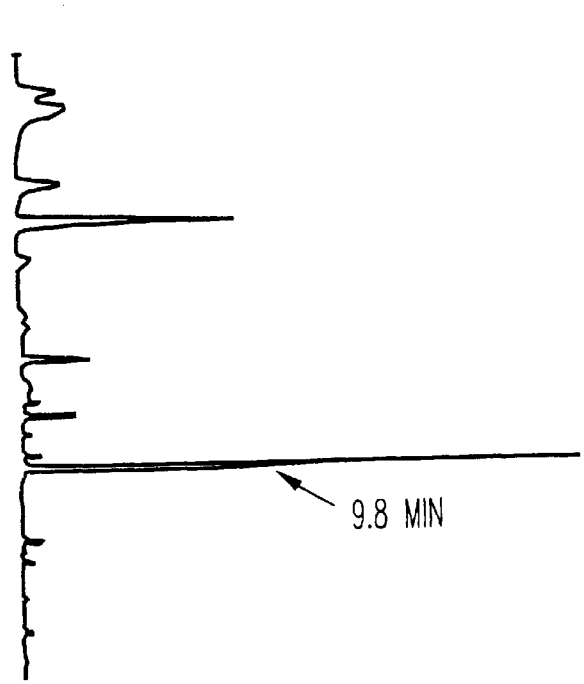
FIG. 10.1
FIG. 10.3
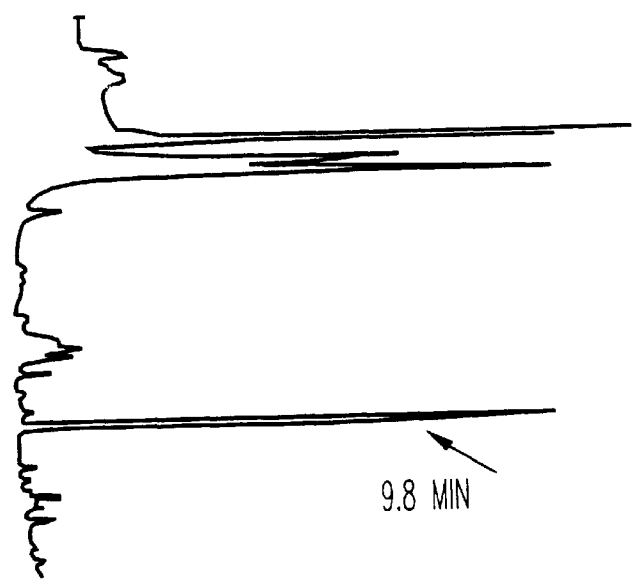
FIG. 10.2

METHOD OF EXAMINING SILANE-TREATED, INORGANIC MATERIALS

BACKGROUND OF THE INVENTION

1. Field of the Invention

The invention relates to a method of examining inorganic materials which have been treated with organosilicon compounds.

2. Discussion of the Background

It is known that hydrophobicization of inorganic materials, in particular mineral building materials, is generally carried out using organosilicon compounds in the form of aqueous emulsions, microemulsions or dissolved in organic solvents (Product Information from Hüls AG: "Anwendungen von organofunktionellen Silanen—DYNASYLAN®", 15.01.002/07.94/gu/100; "Bautenschutz mit Alkylsilanen—DYNASYLAN® BSM", 15.01.006/09.90/gu; Ch. Fliedner, "Silane als Hydrophobierungsmittel für Beton", special publication 15.07.023 of Hüls AG, Parts I and II have appeared in: Bautenschutz+Bausanierung 3/94 and 4/94). On the surface of the inorganic materials, right into the interior of a porous material, reactive groups of the organosilicon compounds form chemical bonds with the hydroxyl groups of the material; in parallel thereto, crosslinking reactions of the silicon compounds occur in the presence of water, which finally leads to a hydrophobicizing film chemically anchored to the surface and even in the pores, which film suppresses or reduces the destructive absorption and transport of water. Examples of building materials which may be mentioned here are concrete, sandstone, lime-sand brick, bricks and mortar. Pulverulent and granular materials such as aluminum oxide, titanium dioxide, magnesium oxide, glass powder and quartz powder, hydroxides, silicates and other mineral products and also glass microspheres are also often surface-modified with organosilicon compounds to improve their application properties.

At present, the testing of surface protection of building materials is carried out by means of water absorption (Technical Testing Instructions for Surface-Protection Systems, 1990 edition, Bulletin, Document No.: B 5234—Test 90.1, page 30), the impregnation depth (exposure of a point to a depth of $\geq 1$ cm and spraying with water), the absorbency profile (water absorption on successively sawn-off slices, M. Roth: Das Wassersaugprofil einer Siliconimprägnierung (The Water Absorbency Profile of a Silicone Impregnation), Bautenschutz und Bausanierung, 11, (1988), pages 43–45), pressure water storage (DIN 52 103) or absorption water storage (DIN 52 617). Decisive factors for the quality of the hydrophobicization are the chemical structure of the hydrophobicizing agent, the amount of active substance absorbed on the surface and in deeper zones and the chemical anchoring of the hydrophobicizing agent on the internal and external surfaces of the building material; virtually no information can be obtained about these factors using the above-mentioned tests, since only the overall water-repellent effect is measured.

Various analytical methods, such as TOF-SIMS (time-of-flight secondary-ion mass spectrometry), ESCA (electron-spectroscopy for chemical analysis), DRIFT (diffuse reflectance infrared Fourier transform) and Auger-electron spectroscopy, have been developed for examining surfaces. Apart from the complex equipment, the large amount of time required and the huge costs, these methods have the disadvantage that usually only the uppermost surface of the test material, in the nanometer range can be measured.

The dispersive IR (infrared spectroscopy) technique is also unsuitable for characterizing silane hydrophobicizing agents under conditions close to practice (Ghosh, S. and Handoo, S. K.: Infrared and Raman Spectral Studies in Cement and Concrete, Cement and Concrete Research, 10, (1980), pages 771–782). However, the penetration depth of hydrophobicizing agents in concrete could be determined by FT(Fourier transform) IR spectroscopy (A. Gerdes, T. Müller and F. H. Wittmann in: Werkstoff-wissenschaften und Bausanierung, Part 1, Symposium Report of the 3rd International Colloquium, edited by F. H. Wittmann, expert publishers (Kontakt & Studium Vol. 420) Ehningen bei Böbblingen, 1993, pages 460–475). Concrete flour milled to analytical fineness is mixed with potassium bromide (1:25) and pressed at 250 bar to give transparent tablets and an FT-IR spectrum was recorded thereon in the absorption range of 2900–2940 $cm^{-1}$. The $CH_2$ stretching vibration in the region of 2930 $cm^{-1}$ serves for the qualitative or semi-quantitative determination of hydrophobicizing agents based on organosilicon compounds, provided that organic compounds which can interfere with the detection are not present. Apart from the complication in terms of equipment and preparation, this method has further disadvantages: the various hydrophobicizing or modifying agents cannot be differentiated; active substance contents below about 0.2% cannot be measured; large particles cannot be analyzed without fine milling; hydrophobicizing agent mixtures are not recognizable as such; covalent fixing and physical coating cannot be differentiated; modifications of, for example, glass beads, aluminum oxide or silicates cannot be detected owing to a lack of sensitivity of the method. $^{29}$Si-MAS-NMR spectroscopy (29-Si magic angle spinning nuclear magnetic resonance spectroscopy) is, due to the high cost and the limited detection sensitivity, also unsuitable for quality testing when using the hydrophobicizing and modifying agents in day-to-day practice; rather, this method is used for fundamental studies (J. Grobe, K. Stoppek-Langner, W. Müller-Warmuth, S. Thomas, A. Benninghoven and B. Hagenhoff: Nachr. Chem. Tech. Lab., 41, (1993), No. 11, pages 1233–1240; B. Hagenhoff, A. Benninghoven, K. Stoppek-Langner and J. Grobe: Adv. Mater., (1994), 6, No. 2, pages 142–144; K. Albert, R. Brindle, J. Schmid, B. Buszewski and E. Bayer: Chromatographia, 38, (1994), pages 283–290).

The pyrolysis of silane-coated fillers, specifically talc, has been utilized for detecting organofunctional silanes used for coating, by pyrolyzing a relatively large amount of filler (10 g) at 720° C. for about 30 minutes; the large amount was necessary to achieve the detection limits of 0.01–0.1% and the long pyrolysis time associated with the "large" amount of sample was necessary to favor secondary reactions (artifact formation) which were to aid the differentiation of individual silanes. The pyrolysis products were collected in an organic solvent (triethylene glycol dimethyl ether) at 0° C. and the absorption solution together with the condensate, which can separate out before the absorber, was subsequently analyzed by gas chromatography (off-line); separation column: 60 m DB wax thin-film capillary, film thickness: 0.5 $\mu$ (R. Doiber and N. Wamser: Fresenius J. Anal. Chem., 342, (1992), pages 381–386). Disadvantages of this method are that reaction products which are characteristic or selective for particular coating agents (ammonia, hydrogen sulphide, acetone) are formed only in exceptional cases and that the major part of the numerous indeterminable pyrolysis products is identical for all silanes, so that only quantitative differences in the gaschromatographic peak distribution can be used for identification. In addition, the alkoxy groups (methoxy or ethoxy groups) characteristic of many hydrophobicizing and modifying agents cannot be detected.

The very complicated and additionally high-cost FT-IR analytical method (pyrolysis gas chromatography with Fourier transform infrared spectroscopy) has been used to establish whether N-phenyl-1-aminopropyltrimethoxysilane in acetic acid is chemically bound or is able to be washed off with methanol in the silane treatment of E glass fibers (N. Ikuta, T. Hori, H. Naitoh, Y. Kera, E. Nishio and I. Abe, Compos. Interfaces (1993), 1(6), 455–462).

Pyrolysis gas chromatography has also been used to examine poly(diorganosiloxanes) (S. Fujimoto, H. Ohtani and S. Tsuge: Fresenius Z. Anal. Chem., 331, (1988), pages 342–350), where numerous cyclic oligomers were mainly formed and these were separated on a thin-film capillary (WCOT column). The quantitative analysis of these oligomers, made possible a determination of the original composition by means of the components, of which there were often more than 19, only by means of a complicated method.

To assess the quality of the hydrophobicization or surface modification of inorganic materials there is a need for a method of examination by means of which the organosilicon compounds used here can be detected as specifically as possible and their concentration on the surface and possibly also at various depths of the inorganic substrate can be determined quantitatively.

It is therefore an object of the invention to provide a method which makes it possible, with justifiable expense, to examine inorganic materials which have been treated with organosilicon compounds for hydrophobicization or surface modification, to identify the organosilicon compounds used very reliably and also to be able to quantify them.

It has surprisingly been found that organosilicon hydrophobicizing and modifying agents on inorganic materials, in particular on and in building materials, can be specifically detected and reproducibly determined quantitatively by, generally, first pyrolyzing the sample material over a period of a few seconds and analyzing the pyrolysis products on-line by gas chromatography on thin-layer capillaries (PLOT (porous layer open tubular) columns, i.e. capillary column and porous layer). A main component preferentially formed in the pyrolysis is conveniently used for identification and quantitative determination.

SUMMARY OF THE INVENTION

The present invention accordingly provides a method of examining inorganic materials which have been treated with organosilicon compounds, comprising pyrolyzing a sample material in the course of a few seconds; and analyzing pyrolysis products on-line by gas chromatography on a porous layer open tubular column, i.e. capillary column having a porous layer.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 1: Conventional gas-chromatographic examination of reaction products which form in the pyrolysis of various alkyltriethoxsilanes on concrete (FIGS. 1.1 to 1.4)

FIG. 1.1: Pyrolysis-gas chromatogram (GC) of 0.4% by weight of methyltriethoxysilane on concrete FIG. 1.2: Pyrolysis-GC of 0.4% by weight of ethyltriethoxysilane on concrete FIG. 1.3: Pyrolysis-GC of 0.4% by weight of propyltriethoxysilane on concrete FIG. 1.4: Pyrolysis-GC of 0.4% by weight of isobutyltriethoxysilane on concrete FIG. 2: Gas-chromatographic examination on a PLOT column 1 according to the method of the invention—pyrolysis of various alkyltriethoxysilanes on concrete (FIGS. 2.1 to 2.4)

FIG. 2.1: Pyrolysis-GC of 0.4% by weight of methyltriethoxysilane on concrete

FIG. 2.2: Pyrolysis-GC of 0.4% by weight of ethyltriethoxysilane on concrete

FIG. 2.3: Pyrolysis-GC of 0.4% by weight of propyltriethoxysilane on concrete

FIG. 2.4: Pyrolysis-GC of 0.4% by weight of isobutyltriethoxysilane on concrete

FIG. 3: Gas-chromatographic examination on a PLOT column 2 according to the method of the invention—pyrolysis of various alkyltriethoxysilanes on concrete (FIGS. 3.1 to 3.4)

FIG. 3.1: Pyrolysis-GC of 0.4% by weight of methyltriethoxysilane on concrete

FIG. 3.2: Pyrolysis-GC of 0.4% by weight of ethyltriethoxysilane on concrete

FIG. 3.3: Pyrolysis-GC of 0.4% by weight of propyltriethoxysilane on concrete

FIG. 3.4: Pyrolysis-GC of 0.4% by weight of isobutyltriethoxysilane on concrete

FIG. 4: Gas-chromatographic examination according to the method of the invention—formation of n-octane in the pyrolysis of n-octyltriethoxysilane on concrete as a function of the pyrolysis temperature in the range from 300 to 900° C. (FIGS. 4.1 to 4.7)

FIG. 4.1: Pyrolysis-GC—pyrolysis temperature 300° C.
FIG. 4.2: Pyrolysis-GC—pyrolysis temperature 400° C.
FIG. 4.3: Pyrolysis-GC—pyrolysis temperature 500° C.
FIG. 4.4: Pyrolysis-GC—pyrolysis temperature 600° C.
FIG. 4.5: Pyrolysis-GC—pyrolysis temperature 700° C.
FIG. 4.6: Pyrolysis-GC—pyrolysis temperature 800° C.
FIG. 4.7: Pyrolysis-GC—pyrolysis temperature 900° C.

FIG. 5: Gas-chromatographic examinations according to the method of the invention—pyrolysis of silanes having different organofunctional groups (FIGS. 5.1 to 5.3)

FIG. 5.1: Pyrolysis-GC of 1% by weight of 3-aminopropyltriethoxysilane (AMEO) on concrete (Pyrolysis temperature: 500°C., Sample weight: 3.050 mg, PLOT column: Pora PLOT Q)

FIG. 5.2: Pyrolysis-GC of 0.5% of 3-methacryloxypropyltrimethoxysilane (MEMO) on concrete (Pyrolysis temperature: 500° C., Sample weight: 5.130 mg, PLOT column: Pora PLOT Q)

FIG. 5.3: Pyrolysis-GC of a mixture of 1% by weight of AMEO on concrete and 0.5% by weight of MEMO on concrete. Sample weight: 4.5 mg of AMEO-doped and 3.1 mg of MEMO-doped concrete (Pyrolysis temperature: 500° C., PLOT column: Pora PLOT Q)

FIG. 6: Examples of calibration curves

FIG. 6.1: Calibration curve for isobutyltriethoxysilane (IBTEO) on concrete

FIG. 6.2: Calibration curve for isobutyltrimethoxysilane (IBTMO) on lime-sand brick

FIG. 8: Determination of a depth profile according to the method of the invention-on the surface, at 4.5 mm depth, at 8 depth and at 18 mm depth of a concrete treated with isobutyltrimethoxysilane (IBTMO).

FIG. 8.1: On the surface (Sample weight: 1.524 mg)

FIG. 8.2: At 4.5 mm depth (Sample weight: 2.471 mg)

FIG. 8.3: At 8 mm depth (Sample weight: 3.684 mg)

FIG. 8.4: At 18 mm depth (Sample weight: 4.109 mg)

FIG. 9: Effect of the extraction on the hydrophobicization of concrete-examinations using a Pora PLOT column containing $Al_2O_3/KCl$ (FIGS. 9.1 to 9.4)

FIG. 9.1: Concrete treated with isobutyltriethoxysilane (at3 mm depth), prior to extraction (Sample weight: 5.362 mg)

FIG. 9.2: Concrete treated with isobutyltriethoxysilane (at 3 mm depth), prior to extraction (Sample weight: 4.111 mg)

FIG. 9.3: Concrete treated with isobutyltriethoxysilane (at 3 mm depth), after exhaustive extraction with n-heptane (Sample weight: 4.821 mg)

FIG. 9.4: Concrete treated with isobutyltriethoxysilane (at 3 mm depth), after exhaustive extraction with n-heptane (Sample weight: 4.943 mg)

FIG. 10: Pyrolysis-GC according to the method of the invention—3aminopropyltrimethoxysilane (AMEO) on various inorganic materials (FIGS. 10.1 to 10.3)

FIG. 10.1: 0.5% by weight of AMEO on concrete (Pyrolysis temperature: 500°C., Sample weight: 6.229 mg, PLOT column: 10 m Pora PLOT Q)

FIG. 10.2: 0.5% by weight of AMEO on hydrated aluminum oxide ($Al_2O_3.3H_2O$) (Pyrolysis temperature: 500° C., Sample weight: 11.752 mg, PLOT column: 10 m Pora PLOT Q)

FIG. 10.3: 5% by weight of AMEO on talc (Pyrolysis temperature: 500°C., Sample weight: 5.351 mg, PLOT column: 10 m Pora PLOT Q)

DETAILED DESCRIPTION OF THE PREFERRED EMBODIMENTS

Figure 7:
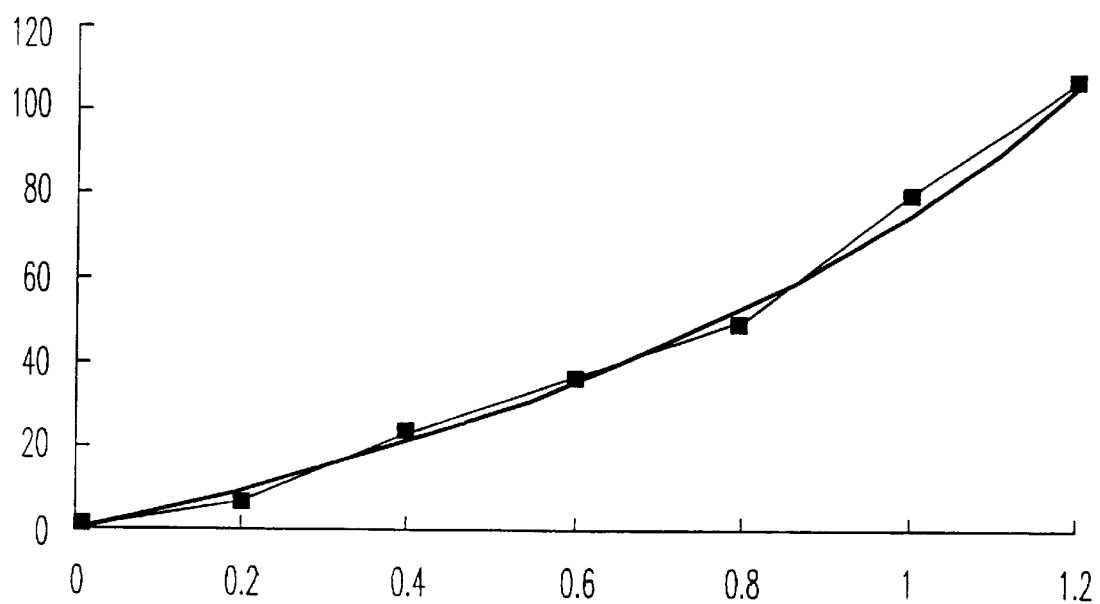
FIG. 7: Calibration curve for 3-methacryloxypropyltrimethoxysilane (MEMO) on quartz powder (cristobalite)

In the method of the invention, the identification of the organosilicon compounds, preferably also their quantitative determination, is conveniently carried out by means of components, i.e. pyrolysis products, which are preferentially formed under the prevailing pyrolysis conditions.

FIG. 1 shows the pyrolysis products of four hydrophobicizing agents (methyl-, ethyl-, propyl- and isobutyltriethoxysilane) which were, in each case, applied to concrete in an amount of 0.4% a by weight and were examined by pyrolysis/gas chromatography in a conventional manner (thinfilm capillary, WCOT column). The differences between the individual building protection agents are only slight and are unsuitable for identification and differentiation of such silane coatings.

FIG. 2 shows the pyrolysis-gas chromatograms of the same samples, as were also used in tests for FIG. 1, but which were examined by the method of the invention; for this purpose, a PLOT column 1 (PoraPLOT Q, length 10 m, internal diameter 0.32 mm, layer thickness 10 $\mu$ (Chrompack GmbH, Frankfurt/Main)) was conveniently used. The surprising thing here is that methyltriethoxysilane on concrete gives virtually only methane as pyrolysis product, ethyltriethoxysilane gives only ethane, propyltriethoxysilane gives mainly propane and isobutyltriethoxysilane gives predominantly isobutane. It is known from $^{29}$Si-NMR examination that on hydrophobicized building material surfaces, predominantly polymeric networks of monofunctional, difunctional and trifunctional polysiloxanes are present as a result of hydrolysis and polycondensation of the monomeric building protection agent (J. Grobe et al., Nachr. Chem. Techn. Lab, 41, (1993), No. 11, pages 1233–1240) and that the numerous chemical surface structures should not lead to the same pyrolysis product.

The pyrolysis time of the sample material is, in the method of the invention, generally less than 10 seconds, preferably from 5 to 0.001 seconds, particularly preferably from 5 to 0.1 seconds.

The pyrolysis of the sample material is carried out by conventional methods known to those of ordinary skill in the art, such as by using, for example, a hot-wire pyrolyzer, a Curie point pyrolyzer, a laser pyrolyzer or a microwave pyrolyzer or another method of inputting energy. Preference is given to using a boat pyrolyzer.

The pyrolysis products are separated by on-line gas chromatography on a PLOT column, preferably without any intermediate step such as adsorption, cold trap technique, low-temperature focusing, column switching technique, and are generally indicated by a detector, preferably by a flame ionization detector.

For the gas-chromatographic examination of the pyrolysis products, use is made of PLOT columns which preferably contain aluminum oxide deactivated by KCl or $Na_2SO_4$, or silica gel or graphitized thermal carbon black or organic polymers based on styrene/divinylbenzene as solid porous layer. Such capillary columns are generally quartz capillaries or suitable metal capillaries having a porous layer of one of the abovementioned materials.

The pyrolysis of the sample material is preferably carried out in the temperature range between 500 and 800° C., but can also be carried out in the temperature range from about 300 to 900°C.. In general, a carrier gas stream, for example a noble gas, preferably helium or argon or neon, is passed over the sample material so that the pyrolysis of the sample material is conveniently carried out in the carrier gas stream of the gas chromatograph. However, oxygen-free nitrogen or hydrogen can also be used as carrier gas in the method of the invention.

FIG. 3 shows the pyrolysis-gas chromatograms of the same samples described for FIG. 2; a PLOT column 2 (25 m long, 0.32 mm internal diameter, layer of $Al_2O_3/KCl$, thickness 5 $\mu$, Chrompack GmbH, Frankfurt/Main) was conveniently used here. Using the pyrolysis arrangement selected here, cf. also the Example 1 according to the invention, the organic radical bonded to silicon can be completely split off at a temperature as low as about 500° C.; here too, the corresponding alkane is the only component which is formed in a relatively large amount as pyrolysis product.

Furthermore, the method of the invention can also be carried out at a pyrolysis temperature of about 800° C.; in general, this does not significantly increase the number and amount of other smaller fragments.

FIG. 4 shows, by way of example, the effect of temperature for the less thermally stable n-octyltriethoxysilane on concrete. The pyrolysis temperature examined was, in particular, the range from 300 to 900° C.: below 500° C, only little splitting off of the octyl radical (which appears as octane) takes place. Above 900° C., this radical is largely decomposed. Here too, the preferred range for the pyrolysis temperature is between 500 and 800° C.; the octyltriethoxysilane applied to concrete and also its hydrolysis, condensation and crosslinking products formed and anchored on or in the concrete surface here decompose preferentially to octane.

It is also possible to carry out the method of the invention on other inorganic materials treated with organosilicon compounds: for example on mineral products, sandstone, limestone, clay-containing or siliceous materials, brick, mortar, pigments, aluminum oxide-containing materials, titanium oxide-containing materials, magnesium oxide-containing materials or corresponding materials, quartz products or quartz powders, glass products such as glass mats, glass fibers, glass beads, glass microbeads, glass powders, optical glasses or insulation materials such as glass wool or rock wool, but also on fillers or metals or alloys. These materials can be present in solid, ductile, pulverulent, granular and/or vitreous oxidic, hydroxidic, carbonatecontaining, metallic and/or siliceous dense and/or porous form.

For the treatment of materials mentioned above by way of example, thermally and chemically unstable silanes can also be used, for example 3-methacryloxypropyltrimethoxysilane (MEMO) and 3-aminopropyltrimethoxysilane (AMMO). In the case of these compounds, pyrolysis in the preferred temperature range of from 500 to 800° C. did not form mainly only small $C_{1-3}$ fragments, but also characteristic high boilers which are astonishingly retained during the pyrolysis process under the conditions of the method of the invention.

FIG. 5.1 shows, by way of example, the pyrolysis-gas chromatogram of a concrete powder doped with 1% of 3-aminopropyltriethoxysilane (AMEO: $H_2N-(CH_2)_3Si(OC_2H_5)_3$) (the main component A has a retention time of 9.133 minutes). FIG. 5.2 shows the pyrolysis-gas chromatogram of a concrete powder sample coated with 0.5% of 3-methacryloxypropyltrimethoxysilane (MEMO: $CH_2=C(CH_3)COO(CH_2)_3Si(OCH_3)_3$) (the retention time of the main component B formed here is 8.743 minutes) and FIG. 5.3 shows the graph obtained from a mixture of AMEO and MEMO on concrete. The assignment of pyrolysis products to the organosilicon compounds used in each case in the sample material for the hydrophobicization or modification is generally not difficult to achieve. Even the alkoxy radical of the silane originally used for coating, for example an organotrimethoxysilane or organotriethoxysilane, can be identified by means of the methanol or ethanol peak which forms as a small secondary component.

In the method of the invention, the organosilicon compounds, i.e. the hydrophobicizing or coating or modifying agents, can be not only identified, but also quantitatively determined by means of components which are preferentially formed under the prevailing pyrolysis conditions.

FIG. 6 shows the calibration curves for isobutyltriethoxysilane (IBTEO) on concrete and for isobutyltrimethoxysilane (IBTMO) on lime-sand brick. The ordinate is the detector signal in mV.min and the abscissa is the number of micrograms of silane pyrolyzed. For example, a sample weight of 3 mg of a concrete containing 2.57% of silane will correspond to an absolute amount of 77 μg of silane and would give a detector signal of 22.3 mV.min for the characteristic pyrolysis product isobutane, and 30 mg of a concrete containing 0.01% of IBTEO (=3 μg of IBTEO) would give a detector signal of 1.8 mV.min (both points are plotted on the upper curve). The area of the pyrolysis peak characteristic of the silane used can thus be used for determining the silane concentration over a wide range by variation of the sample weight.

The concentration of the organosilicon compounds applied to inorganic materials or introduced therein for the purposes of hydrophobicization or modification or their subsequent or hydrolysis or condensation products is usually from about 5 to 0.01% by weight, based on the sample material present, but the concentrations can also be higher or lower.

The repeatability standard deviation of the determination of building protection agents is about 0.12, the repeatability is 0.34 and the coefficient of variation at a mean value of, for example, 1.5% of hydrophobicizing agent is 8%.

A further calibration curve (3-methacryloxypropyltrimethoxysilane, MEMO) on quartz powder (cristobalite) is shown in FIG. 7, in which the peak areas measured by an integrator in counts/mg of sample are plotted against the percentages by weight.

It has also been found that the inorganic material on which the silanes are applied (for hydrophobicizations, e.g. concrete, lime-sand brick, face bricks, for coatings, e.g. quartz, glass, metal powder, aluminum oxide, titanium dioxide, etc.) can influence the pyrolysis. For this reason, the calibration curves are conveniently set up using a largely comparable material, preferably using the same material.

In the method of the invention, the substrate influence on the pyrolysis can be largely eliminated by preferably pyrolyzing a part of the sample material, determining the blank value for the pyrolysis residue according to the invention, then treating the pyrolysis residue with an organosilicon-containing comparison compound and examining it again.

In view of the sample amounts pyrolyzed in the method of the invention, the sample should be as homogeneous as possible good mixing is therefore to be preferred in the case of powders. In the method of the invention, the pyrolysis is carried out using preferably from 0.1 mg to 500 mg, particularly preferably from 0.5 mg to 100 mg, very particularly preferably from 1 mg to 50 mg, of sample material which conveniently has a content of organosilicon compounds of from 5 to 0.01% by weight.

For determining the penetration depth into a porous material, for example in the case of building materials such as concrete or lime-sand brick, a convenient procedure is to take samples from a sample body at the surface and/or at various depths by careful grinding, boring or milling and to examine these according to the teachings of the present invention.

For this purpose, the sample body can also be clamped in a suitable holding fixture, test material taken off the surface and also at the depths to be tested in the test body (e.g. at depths of 1 mm, 2 mm, 4 mm, 8 mm or even more frequently and at lesser or greater intervals) using, for example, a microgrinder for parting-off (e.g. diamond parting wheel, diameter 10–30 mm, grinding width 0.1–0.2 mm) or a microborer (diamond borer, diameter $\leq 1$ mm), in such a way that preferably about 10–100 mg of powder are obtained, and the examination of the sample material can subsequently be carried out by the method of the invention.

The pulverulent material collected separately for each penetration depth is preferably freed of excessively coarse fragments (to ensure homogeneity), well mixed and a sub-sample thereof is analyzed. During the grinding or boring or milling, care should be taken to ensure that the rotational speed of the grinding wheel, the borer or the milling cutter is kept as low as possible to avoid excessive heating of the material to be ground off. From the active substance concentrations determined by means of pyrolysis/gas chromatography and the depths from which the samples were taken, an active substance profile (concentration plotted against the depth) can be constructed.

Since it is decisive for the quality of building protection whether the hydrophobicizing agents are lying only physically on the external and internal surfaces and can therefore be washed out or whether they are chemically bound to the surface and thereby ensure a durable impregnation, it is advantageous to analyze the respective samples as described above and additionally to extract parts of the sample, prior to pyrolysis, with a suitable solvent, for example n- or i-pentane, n- or i-hexane or cyclohexane, n- or i-heptane, n- or i-octane or toluene, xylenes or methanol, ethanol or methylene chloride or trifluorotrichloroethane (R-113) or other chlorinated hydrocarbons or chlorofluorocarbons, dry it and then analyze it (cf. also Example 3).

The method of the invention can thus also provide additional information about the bonding character of hydrophobicizing or modifying agents after treatment of an inorganic material if, conveniently, at least one subsample of the sample material is extracted prior to pyrolysis with a solvent, dried and then separately pyrolyzed and analyzed.

The method of the invention makes it possible, in a simple and economical manner, to detect, identify and very largely quantify reliably silane-containing hydrophobicizing agents and modifying agents on inorganic materials, in particular building materials. Furthermore, the method of the invention also makes it possible, in a simple and reliable manner, to determine the penetration depth of the materials thus hydrophobicized or modified using organosilicon compounds.

Having generally described this invention, a further understanding can be obtained by reference to certain specific examples which are provided herein for purposes of illustration only and are not intended to be limiting unless otherwise specified.

The invention is illustrated in more detail by the following examples and the FIGS. 1 to 10:

EXAMPLE 1

From a concrete sample hydrophobicized with isobutyltrimethoxysilane (IBTMO) (120 g/m$^2$), which had been drilled out of a hydrophobicized concrete wall and was in the form of a cylindrical body, about 20 mg in each case of concrete powder were ground out of the surface, 4.5 mm below, 8 mm below and 18 mm below the surface using a diamond parting wheel (wheel thickness 0.1 mm). Care was here always taken to ensure that the rotation rate of the parting wheel remained low so as to prevent premature decomposition of the hydrophobicizing agent, and that no pebbles (which hardly absorb hydrophobicizing agent) present in the concrete were ground off but that a fairly representative concrete composition was ground off at various points of the respective depth. The respective samples from the various depths were individually thoroughly mixed and relatively large fragments which could cause inhomogeneities were sorted out and discarded.

About 1–5 mg of the ground-off powder were accurately weighed into a platinum boat fitting into a pyrolyzer PYR-2 from Shimadzu Europa GmbH and pyrolyzed at 700° C., by pushing a push rod together with the microboat into the 700° C. zone and, on-line, immediately flushing the pyrolysis products suddenly formed into the gas-chromatographic separation column using the carrier gas helium. The pyrolysis products were separated there and registered by a flame ionization detector.

Separation column: 10 m quartz capillary PoraPLOT Q,
Internal diameter: 0.32 mm,
Layer thickness: 10 µm, Chrompack GmbH, Frankfurt/Main.

Temperature program: 60° C./2 min isothermal, 10° C./min to 120° C., 9 min isothermal.

The corresponding gas chromatograms are shown in FIG. 8.

From the peak areas (counts or mV.min), based on the sample weight, the percentages by weight of active substance on concrete were calculated with the aid of a calibration curve: Surface 1.05%, 4.5 mm depth: 0.36%, 8 mm depth: 0.14%, 18 mm depth: <0.01%.

The calibration curve (e.g. FIGS. 6 and 7) is obtained in the following manner:

About 200 mg of a suitable concrete are ground off. After checking that the concrete does not give off, under the conditions of the pyrolysis/gas chromatography, any organic constituents which interfere with the evaluation, 20 mg samples thereof are weighed into a bottle having a rim, admixed with different concentrations of an ethanolic (organoethoxysilanes) or methanolic (organomethoxysilanes) solution of the silane in question, closed and allowed to stand for 24 hours at room temperature. The solvent (methanol or ethanol) is then blown off in a stream of nitrogen (fume cupboard) and the now dry residue is kept open for 30 minutes at 70° C. in a drying oven to drive off remaining traces of alcohol. The individual samples are pyrolyzed and the peak areas of the respective main peak are plotted against the amount of organoalkoxysilane (µg, calculated from amount applied and sample weight, FIG. 6) or the peak areas per mg of sample weight are plotted against the organoalkoxysilane concentration (% by weight of organoalkoxysilane on concrete, FIG. 7) and the curve is constructed.

EXAMPLE 2

To determine whether the hydrophobicizing agent is present in chemically bound form or is only physically adsorbed, the following procedure was carried out:

150 mg of a concrete hydrophobicized with isobutyltriethoxysilane were carefully ground out from a depth of 3 mm and 5.362 mg or 4.111 mg thereof were analyzed using a method similar to Example 1 (FIGS. 9.1 and 9.2).

The separation column used here was a 25 m quartz capillary PoraPLOT Al$_2$O$_3$/KCl, internal diameter: 0.32 mm, layer thickness: 5 µm, from Chrompack GmbH, Frankfurt/Main.

Temperature program: 60° C./2 min isothermal, 12° C./min to 180° C., 12 min isothermal. 0.40% by weight of active substance was found.

In parallel thereto, 125 mg of the same concrete powder were extracted with 40 ml of n-heptane (Bp. 98° C.) for 3.5 hours in a micro-Soxhlet and then freed of residual heptane for 1 hour in a vacuum drying oven at 90° C. and a further hour in a normal drying oven at 80° C. Two pyrolysis-gas chromatographic analyses were likewise carried out on this extracted concrete (sample weights: 4.821 or 4.943 mg, FIGS. 9.3 and 9.4). Result: 0.39% by weight of active substance, i.e. 97.5% of the isobutyltriethoxysilane are accordingly bound to concrete and therefore not extractable, and only 2.5% are in physically adsorbed form. Corresponding to this result, the pyrolysis-gas chromatograms of the extracted samples (FIG. 9.3 and FIG. 9.4) differ very little from those of the unextracted samples (FIGS. 9.1 and 9.2).

EXAMPLE 3

Examination of pulverulent, mineral materials:

Depending on the expected silane concentration, about 1 mg (at >2% by weight) to 50 mg (at <0.02% by weight) are accurately weighed out and pyrolyzed as described. Since, in contrast to the building protection agents which are predominantly alkylalkoxysilanes, the coating is carried out using predominantly organofunctional alkoxysilanes such as, for example, acryloxypropyl-, 3-methacryloxypropyl-, glycidoxypropyl-, 3-aminopropyl-trialkoxysilanes which bear a chemically and thermally-less stable organic group, the influence of the substrate on the pyrolysis is also stronger. This is shown in FIGS. 10.1 to 10.3, where the same silane (3-aminopropyltrimethoxysilane) had been applied to concrete powder (FIG. 10-1), hydrated aluminum oxide $Al_2O_3.3\ H_2O$ (FIG. 10.1) and talc (FIG. 10.3) respectively. The characteristic largest relatively high-boiling pyrolysis product (retention time 9.8 minutes) did occur in each case, but lower-boiling dissociation products are represented to a differing extent depending on the activity of the substrate: the component having the retention time of 7.2 minutes, for example, (n-propanol) occurs predominantly in the case of talc, but only in traces in the case of the more active aluminum oxide. For this reason, it is advisable to proceed as follows if such silanes could be present:

A part of the sample is pyrolyzed at 700° C. To check whether the pyrolyzable components had been completely decomposed, a few milligrams of the sample are again subjected to a pyrolysis, but at 500° C. If this material, as expected, gives only a negligibly small blank value, it is covered with an alcoholic solution of the presumed silane, allowed to stand for 24 hours to react, the alcohol is driven off and the entire material is dried for a further 30 minutes at 70° C. in a drying oven. Pyrolysis is then carried out at 500° C. and the pyrolysis gas chromatogram is compared with the unknown sample. If the two are in agreement, different amounts of silane are then applied to the material pyrolyzed at 700° C. and, as already described, a calibration curve is constructed. In this way, the substrate corresponds completely to that of the sample to be examined, and erroneous interpretations caused by substrate effects can be avoided.

Obviously, numerous modifications and variations of the present invention are possible in light of the above teachings. It is therefore to be understood that within the scope of the appended claims, the invention may be practiced otherwise than as specifically described herein.

This specification is based on German patent application 195 14 033.8 filed in the German Patent Office on Apr. 13, 1995, the entire contents of which are hereby incorporated by reference.

What is claimed as new and desired to be secured by Letters: Patent of the United States is:

1. A method for examining inorganic materials which are treated with organosilicon compounds, comprising pyrolyzing a sample material; and analyzing pyrolysis products on-line by gas chromatography on a porous layer open tubular column.

2. The method of claim 1, wherein identification of said organosilicon compounds is carried out by analysis of components which are preferentially formed under the prevailing pyrolysis conditions.

3. The method of claim 1, wherein a quantitative determination of said organosilicon compounds is carried out by analysis of components which are preferentially formed under the prevailing pyrolysis conditions.

4. The method of claim 1, wherein pyrolysis of said sample material is carried out at a temperature range between 500° C. and 800° C.

5. The method of claim 1, wherein pyrolysis of said sample material is carried out in a carrier gas stream which is the same as a carrier gas stream of said gas chromatograph.

6. The method of claim 1, wherein a pyrolysis time of said sample material is less than 10 seconds.

7. The method of claim 1, wherein from 0.1 mg to 500 mg of said sample material are used for pyrolysis.

8. The method of claim 1, wherein said sample material has an organosilicon compound content of from 5 to 0.01% by weight.

9. The method of claim 1, wherein said porous layer open tubular column comprises as a solid porous layer a material selected from the group consisting of aluminum oxide deactivated by KCl or $Na_2SO_4$, silica gel, graphitized thermal carbon black and organic polymers based on styrene/divinylbenzene.

10. The method of claim 1, wherein said sample material is separately taken from a sample body at the surface, at various depths or both by careful grinding, boring or milling and separately analyzed.

11. The method of claim 1, further comprising extracting at least one subsample of said sample material, with a solvent prior to the pyrolysis, drying and then separately pyrolyzing and analyzing said substrate.

12. The method of claim 1, further comprising calibration by pyrolyzing a part of said sample material, determining a blank value of pyrolysis residue, then treating said pyrolysis residue with an organosilicon-containing comparison compound and examining it again.

13. The method of claim 1, wherein pyrolysis is conducted with a device selected from the group consisting of a boat-pyrolyzer, a hot-wire pyrolyzer, a Curie point pyrolyzer, a laser pyrolyzer or a microwave pyrolyzer.

14. The method of claim 1, wherein pyrolysis of said sample material is carried out at a temperature range between 300° C. and 900° C.

15. The method of claim 1, wherein said porous layer open tubular column is a capillary column having a porous layer.

* * * * *